United States Patent
Borod

(10) Patent No.: US 6,228,387 B1
(45) Date of Patent: May 8, 2001

(54) INTEGRATED COMPREHENSIVE HEMORRHOID TREATMENT COMPOSITIONS AND REGIMEN

(76) Inventor: Murray Borod, 1420 Capri Ave., Petaluma, CA (US) 94954

( * ) Notice: Subject to any disclaimer, the term of this patent is extended or adjusted under 35 U.S.C. 154(b) by 0 days.

(21) Appl. No.: 09/641,884

(22) Filed: Aug. 18, 2000

Related U.S. Application Data

(60) Provisional application No. 60/177,665, filed on Jan. 27, 2000.

(51) Int. Cl.[7] .............................. A01N 65/00; A61F 9/02; A61K 9/48
(52) U.S. Cl. ..................... 424/436; 424/195.1; 424/451; 424/452
(58) Field of Search .............................. 424/195.1, 436, 424/452

(56) References Cited

U.S. PATENT DOCUMENTS

| | | | |
|---|---|---|---|
| 4,169,143 | * | 9/1979 | Haimowitz et al. ................. 424/284 |
| 4,178,372 | | 12/1979 | Coats . |
| 4,698,360 | | 10/1987 | Masquelier . |
| 4,761,285 | | 8/1988 | Vasiliou et al. . |
| 4,767,618 | | 8/1988 | Grollier et al. . |
| 4,925,871 | | 5/1990 | Gabetta et al. . |
| 4,938,960 | | 7/1990 | Ismail . |
| 5,266,318 | | 11/1993 | Taylor-McCord . |
| 5,470,874 | | 11/1995 | Lerner . |
| 5,587,149 | | 12/1996 | Punto et al. . |
| 5,665,365 | * | 9/1997 | Bombardelli et al. ............ 424/195.1 |
| 5,698,206 | | 12/1997 | Becker et al. . |
| 5,804,168 | | 9/1998 | Murad . |
| 5,849,338 | | 12/1998 | Richardson et al. . |
| 5,869,059 | * | 2/1999 | Garza ................................ 424/195.1 |
| 5,916,573 | | 6/1999 | Spiers et al. . |
| 6,083,507 | * | 7/2000 | Belle et al. ........................ 424/195.1 |

OTHER PUBLICATIONS

The Healing Powerof Herbs, 2nd ed., M.T. Murray (Prima Publishing, Rockin, CA 1995), pp. 173–183, 365, 385–386.
The Healing Power Of Vitamins, Minerals and Herbs, (Readers Digest Association, Ltd., Pleasantville, NY 1999), pp. 138–139, 244–245, 306–307.

* cited by examiner

*Primary Examiner*—Herbert J. Lilling
(74) *Attorney, Agent, or Firm*—Richard C. Litman

(57) ABSTRACT

A first composition for topical application and a second for oral administration, make up a comprehensive program for the treatment and relief of hemorrhoids. The topical application composition contains supplements for healing of hemorrhoids including an agent for the enhancement of the formation of collagen and elastin, an antioxidant having a proanthocyanidin as the active agent in combination with vitamin C, one or more anti-inflammatory agents, and vitamin E. In the preferred embodiment, the composition is made from gotu kola extract, grape seed extract, horse chestnut extract, aloe vera, vitamin C, and vitamin E. A few drops each of Essential Oils of Chamomile and Lavender may be included. The composition may be formulated as an ointment, cream or gel for external application. The components of the composition work synergistically to relieve the pain, discomfort and swelling associated with hemorrhoids while enhancing the connective tissue sheathes surrounding and supporting the veins and capillaries. The composition for topical application is used in combination with a second composition of supplements for oral administration which includes gotu kola extract, grape seed extract, bilberry extract, vitamin C and vitamin E. The second composition is administered as a daily dosage, and may be formulated as one or more tablets, capsules, softgels or gelcaps.

8 Claims, No Drawings

INTEGRATED COMPREHENSIVE HEMORRHOID TREATMENT COMPOSITIONS AND REGIMEN

CROSS-REFERENCE TO RELATED APPLICATION

This application claims the benefit of U.S. Provisional Patent Application Serial No. 60/177,665, filed Jan. 27, 2000.

BACKGROUND OF THE INVENTION

1. Field of the Invention

The present invention relates generally to hemorrhoid treatment and relief, and more specifically to a comprehensive, integrated treatment regimen and relief of pain and discomfort, including separate compositions that promote healing from inside and outside the body. The compositions of the invention are made from vitamins and plant extracts, and include both a topical application composition and a regimen for oral administration.

2. Description of Related Art

Hemorrhoids, sometimes referred to as piles, is a common affliction among both adults and children. The term refers to varicosities of the veins of the hemorrhoidal plexus, characterized by abnormal dilation, knotting, and tortuosity. They may be complicated by inflammation, clotting, and bleeding. A variety of factors have been implicated in causing hemorrhoids, including excessive strain during defecation, prolonged sitting or standing, constipation, overweight, pregnancy, and the normal aging process. Whatever the cause, however, hemorrhoid sufferers experience pain, itching, and discomfort.

When the hemorrhoidal condition is mild to moderate, a conservative course of treatment will usually include stool softeners (such as increased dietary fiber or psyllium seed), sitz baths, and topical analgesics. While such topical analgesics and stool softeners may relieve the patient's symptomatic complaints, they do not actively attempt to alleviate weakness of the veins and capillaries which may either cause or result from constant or repeated stretching and dilatation of the blood vessels of the hemorrhoidal plexus. A return to the normal strength, elasticity, and permeability of the rectal blood vessels may require the formation of collagen and elastin, a process which may be hindered by free radicals and other oxidants in the blood system which occur with aging, dietary insufficiencies, and disease processes.

The present invention addresses this need with a two part treatment regimen so as to treat the disorder from inside the body and on the outside as well. Accordingly, the invention provides a composition for topical application to hemorrhoids made from plant extracts and vitamins, and oral administration of a second composition containing plant extracts and vitamins. It is the simultaneous treatment inside and outside the body that provides the desired relief from hemorrhoids.

Several patents and publications describe the use of plant extracts and vitamins in formulations for treating or alleviating hemorrhoids, skin conditions, and vascular disorders.

U.S. Pat. No. 4,761,285, issued Aug. 2, 1988 to Vasiliou, et al., describes a composition for the relief and treatment of hemorrhoids made from Leptandra Culver's root, chick peas and grape seeds. The composition may be taken orally or made into a salve by the addition of olive oil. U.S. Pat. No. 5,698,206, issued Dec. 16, 1997 to Becker, et al., discloses a composition for the topical treatment of varicose veins composed of a variety of herbs and including 0.01% by volume vitamin E. The effects of the composition may be enhanced by taking vitamin C orally.

U.S. Pat. No. 4,178,372, issued Dec. 11, 1979 to B. C. Coats, teaches a method of stabilizing aloe vera gel for use in facial skin and cosmetic preparations. U.S. Pat. No. 5,266,318, issued Nov. 30, 1993 to D. Taylor-McCord, describes a topical skin formulation for skin damaged by radiation which contains anthraquinone-free aloe vera gel, allantoin and lavender oil. U.S. Pat. No. 4,767,618, issued Aug. 20, 1988 to Grollier, et al., discloses a composition for the cosmetic treatment of hair or skin having between 5–30% by weight powdered plant particles and a cohesive agent, which may be a solvent, fatty body, thickening agent, emulsifier or an emulsion.

U.S. Pat. No. 4,938,960, issued Jul. 3, 1990 to R. Ismail, describes an agent for the treatment of skin containing a high dose of vitamin E with either a blood circulation promoting agent or a vasodilator, and which may optionally include vitamin C. U.S. Pat. No. 5,470,874, issued Nov. 28, 1995 to S. Lerner, teaches topical application of a preparation which includes ascorbic acid (Vitamin C) and up to 5% proanthocyanidin (pycnogenol) derived from pine bark. U.S. Pat. No. 5,587,149, issued Dec. 24, 1996 to Punto, et al., discloses an emulsion for topical application to the skin packaged in a gelatin capsule which has a first phase including Vitamin C dissolved in polyethylene glycol and a second phase having a silicone oil fluid. One example shows pycnogenol in the first phase and Vitamin E in the second phase.

U.S. Pat. No. 5,804,168, issued Sep. 8, 1998 to H. Murad, describes a pharmaceutical preparation for protection of the skin from UV radiation, preferably for oral administration, having (1) at least one antioxidant, which could be Vitamin C or grape seed extract; (2) at least one anti-inflammatory agent, which could be Vitamin E; and (3) at least one immunity boosting component selected from a variety of herbs. U.S. Pat. No. 5,916,573, issued Jun. 29, 1999 to Spiers, et al., discloses a composition for topical treatment of the skin containing about one to ninety-nine percent grapeseed oil (but not a grapeseed extract, Spiers espousing the theory that proanthocyanidins lose their therapeutic effect when hydrated), a hydrating agent (which may be aloe vera and Vitamin E), and deionized water. The preparation is for moisturizing the skin and protecting the skin against free radicals produced by UV radiation.

U.S. Pat. No. 4,925,871, issued May 15, 1990 to Gabette, et al., teaches a method of treating vascular diseases with proanthocyanidin A2, which is extracted from seeds, branches, or the cortex of a tree. U.S. Pat. No. 5,849,338, issued Dec. 15, 1998 to Richardson, et al., discloses compositions containing magnesium for the treatment of vasoconstriction, the compositions optionally containing Vitamins C and E.

U.S. Pat. No. 4,698,360, issued Oct. 6, 1987 to J. Masquelier, discloses a method of preventing and fighting the harmful biological effect of free radicals by administering the extracted proanthocyanidin content from a plant, specifically maritime pine bark (*Pinus maritima*), in an amount effective to reduce harmful free radical effect. The extract is taken from pine bark and reduced to a powder which may be administered orally, intravenously, or as an ointment. This composition has been marketed under the trademark name Pycnogenol®, a registered trademark of Horphag Overseas, Ltd.

A regimen of supplements for hemorrhoids is suggested in *The Healing Power of Vitamins, Minerals and Herbs,*

(Readers Digest Association, Ltd., Pleasantville, N.Y., 1999) at pp. 138–139, which includes 1,000 mg Vitamin C, 500 mg of flavonoids, and 150 mg of butcher's broom three times daily. The same work recommends bilberry extract for the pain and burning of hemorrhoids at pp. 244–245. In *The Healing Power of Herbs,* 2nd ed., M. T. Murray (Prima Publishing, Rockin, Calif., 1995), at pp. 365, 385–86, the herbs gotu kola, grape seed extract, bilberry extract, and the herb butcher's broom in combination with Vitamin C are recommended for hemorrhoids.

None of the above inventions and patents, taken either singly or in combination, is seen to describe the instant invention as claimed.

SUMMARY OF THE INVENTION

The invention is a comprehensive, integrated hemorrhoidal treatment and relief program. The invention has two important components, these being a first composition for topical application, and a second, equally important, composition of supplements for oral administration.

The topical application composition for hemorrhoidal treatment and relief contains supplements for healing of hemorrhoids including an agent for the enhancement of the formation of collagen and elastin, an antioxidant having a proanthocyanidin as the active agent in combination with vitamin C, and an anti-inflammatory agent in combination with vitamin E. In the preferred embodiment, the composition is made from gotu kola extract, grape seed extract, horse chestnut extract, aloe vera, vitamin C, and vitamin E. In addition the composition may include a few drops each of Essential Oil of Chamomile and Essential Oil of Lavender. The composition is a unique product which may be formulated as an ointment, cream or gel for external application. The components of the composition work synergistically to relieve the pain, discomfort and swelling associated with hemorrhoids while enhancing the connective tissue sheathes surrounding and supporting the veins and capillaries.

The composition for topical application is used in combination with a second composition of supplements for oral administration which includes gotu kola extract, grape seed extract, bilberry extract, vitamin C and vitamin E. The second composition is a unique product, a daily dosage which may be formulated as any number of either tablets, capsules, softgels or gelcaps. Together the two compositions replenish deficiencies, particularly vitamin C required for collagen formation and flavonoids for protecting vitamin C, in order to heal hemorrhoids.

Accordingly, it is a principal object of the invention to provide a composition composed of vitamins and plant extracts which may be applied topically or rectally for the relief of pain, swelling and discomfort associated with hemorrhoids and which actively promotes healing through correcting deficiencies.

It is another object of the invention to provide a composition for the treatment and relief of hemorrhoids which provides symptomatic relief and which promotes restoration of the strength, elasticity and permeability of the blood vessels by correcting deficiencies.

It is a further object of the invention to provide a composition for the treatment and relief of hemorrhoids which includes a strong antioxidant component to prevent further oxidative damage due to free radicals.

Still another object of the invention is to provide a composition for the treatment and relief of hemorrhoids whose effectiveness is enhanced by an equally important regimen of daily supplements.

It is an object of the invention to provide improved elements in a therapeutic composition for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENTS

The invention is a comprehensive, integrated hemorrhoidal treatment and relief program, made up of two important components, these being a first composition for topical application, and a second, equally important, composition of supplements for oral administration.

1. Composition for Topical Application

The topical application composition is composed of an agent for the enhancement of the formation of collagen and elastin, an antioxidant having a proanthocyanidin as the active agent in combination with vitamin C, and an anti-inflammatory agent in combination with vitamin E.

The agent for the enhancement of the formation of collagen and elastin is preferably gotu kola (*Centella asiatica*) extract. Gotu kola is described in *The Healing Power of Vitamins, Minerals and Herbs,* (Readers Digest Association, Ltd., Pleasantville, N.Y., 1999) at pp. 306–307 and *The Healing Power of Herbs,* 2nd ed., M. T. Murray (Prima Publishing, Rockin, Calif., 1995), at pp. 173–183. (The foregoing is incorporated into this disclosure by reference.) Centella is a perennial plant native to India, China, Madagascar, Africa and Australia. Gotu kola extract contains a number of pharmacologically active triterpene compounds, including asiatic acid, madecassic acid, asiaticoside, and madecassoside. In addition, gotu kola contains the flavonoids kaempferol, quercetin, and their glycosides. As used in the present invention, the gotu kola extract is preferably standardized to contain at least 10% asiaticoside. Numerous studies have shown gotu kola to be effective in the treatment of varicose veins. Gotu kola appears to aid the formation of collagen and elastin, resulting in improved strength of the connective tissue sheath surrounding the veins and capillaries, reduction in hardening and improved elasticity of the blood vessels, improved blood flow through the veins and capillaries, and improved permeability of the vessel walls.

The antioxidant used in the composition of the present invention is preferably grape seed extract, although Pycnogenol® may be used in alternative embodiments. Both grape seed extract and Pycnogenol contain proanthocyanidins, which are a group of polyphenols having a flavonoid structure, and particularly are made from chains of catechins and epicatechins, resulting in at least ten hydroxyl groups.

The proanthocyanidins are powerful antioxidants, and therefore useful in scavenging free radicals, primarily $O_2^-$, hydrogen peroxide, and hydroxyl radicals. Free radicals are formed in the hemorrhoid sufferer, either as the result of dietary insufficiencies, stress, inflammation or aging. Free radicals are highly reactive and damage the connective tissue and the blood vessels. Proanthocyanidins neutralize free radicals, either by reducing them directly, or by an addition reaction in which the proanthocyanidin is oxidized by the free radicals to incorporate the additional oxygen into their structure. Proanthocyanidins are flavonoids which are thought to enhance vitamin C concentrations in the blood and to promote vitamin C's role in the formation of collagen.

Grape seed extract is preferred to Pycnogenol® because (1) grape seed extract contains a higher proanthocyanidin concentration than Pycnogenol® (about 10% higher); (2) grape seed extract contains the gallic esters of proanthocyanidins, which are regarded as the best free radical scavengers; and (3) grape seed extract may be more economically produced than Pycnogenol. In the preferred embodiment of the present invention, the grape seed extract is standardized to contain 92 to 95% proanthocyanidins.

The main pharmacological constituent of horse chestnut seeds, twigs, sprouts and leaves is the saponin escin or aescin, a mixture of triterpene saponins. Aescin is known to have anti-inflammatory and edemic actions, and is used in topical ointments. Topical gels are standardized to contain 2% aescin.

The composition further contains vitamin C (ascorbic acid). Vitamin C is known to strengthen capillaries and cell walls, and is crucial to the formation of collagen. Vitamin C works synergistically with the powerful antioxidant agent, either grape seed extract or Pycnogenol. The proanthocyanidins in the antioxidant agent serve to protect vitamin C, thereby enabling the vitamin C to perform its role in forming collagen in order to strengthen the blood vessels.

The composition also contains an additional anti-inflammatory agent, preferably aloe vera. Aloe vera is a succulent plant of the Lily family which is native to Africa and grown commercially in warm regions throughout the world. The inner layer of the plant leaf contains a clear gel. Aloe vera gel is known to contain a number of anti-inflammatory agents useful for topical applications. The gel produces anti-inflammatory, moisturizing and emollient effects which help to relieve pain and stop itching. Aloe vera—dilates capillaries allowing more blood to get to the diseased area, thus speeding up the healing process.

The composition contains vitamin E, which is reported to have anti-inflammatory effect when applied topically. Vitamin E, either an α-tocopherol or mixed tocopherols, is also an antioxidant. Studies have shown that vitamin E appears to work synergistically with vitamin C, so that vitamin E helps to maintain vitamin C levels, and vice versa.

If desired, the composition may include a few drops of Essential Oil of Chamomile. Used externally, chamomile is known to help soothe skin inflammation and chamomile contains bacteria-fighting compounds that may speed the healing of infections as well.

Also, the composition may include a few drops of Essential Oil of Lavender, which has properties similar to those of chamomile, and is quite soothing to the skin.

The inventive concept of the composition according to the present invention is intended to extend to any composition containing an agent for the enhancement of the formation of collagen and elastin, an antioxidant having a proanthocyanidin as the active agent in combination with vitamin C, and an anti-inflammatory agent in combination with vitamin E. A preferred example of percentage content of the composition is listed in Table 1 below, although the invention is not limited to the percentages supplied in the table.

TABLE 1

Composition for Topical Application

| Component Supplements | Daily Dosage |
| --- | --- |
| Gotu kola extract, standardized | 40–100 mg |
| Grape seed extract, standardized | 40–100 mg |
| Horse Chestnut Extract, standardized | 40–100 mg |

TABLE 1-continued

Composition for Topical Application

| Component Supplements | Daily Dosage |
| --- | --- |
| Aloe vera gel | 40–100 mg |
| Vitamin C | 30–60 mg |
| Vitamin E | 50–200 IU |
| Essential Oil of Chamomile | a few drops |
| Essential Oil of Lavender | a few drops |

The composition may be made in the form of an ointment, a cream, or a gel. For this purpose, the composition may contain a pharmaceutically acceptable topical carrier which has substantially non-irritating compatible components, either alone or in mixtures, which are suitable for delivering the active components topically. Thus, the composition may contain solvents, fatty bodies, thickening agents, emulsifiers, an emulsion, or other excipients which do not alter the therapeutic effect of the active ingredients. The composition may be packaged in jars, squeeze tubes, suppositories, pads, or in wipes infused with the formula which may be used in place of toilet tissue. Since the components of the composition are soluble, they will be absorbed through the hemorrhoidal tissues and tissues of the anal-rectal region, entering the blood stream through the capillaries. Thus, although the composition is applied topically, the composition will also have systemic effects.

2. Composition for Oral Administration

The effectiveness of topical application of the composition is accompanied by an equally important, daily regimen of a second composition of supplements administered orally. A preferred regimen of supplements is set forth in Table 2 as follows. For purposes of this application, the oral regimen of supplements can be in the form of one or more tablets, capsules, softgels or gelcaps containing the component nutrients in the approximate dosages listed in Table 2.

TABLE 2

Oral Regimen of Supplements

| Supplement | Daily Dosage |
| --- | --- |
| Gotu kola extract, standardized | 100–300 mg |
| Grape seed extract, standardized | 100–300 mg |
| Bilberry extract, standardized | 100–300 mg |
| Vitamin C | 250–1000 mg |
| Vitamin E | 250–1000 I.U. |

The preferred regimen should be administered orally, daily. The dosages may be formulated as one or more tablets, capsules, softgels or gelcaps. For this purpose, the second composition may additionally contain fillers and other excipients.

Bilberry, or *Vaccinium myrtillus,* is a shrubby perennial plant of the berry family endogenous to Europe. The active ingredients in bilberry are flavonoid compounds known as anthocyanosides, which are composed of an anthocyanidin and a sugar. The flavonoids are known to have an antioxidant effect and to work synergistically to maintain vitamin C levels. Bilberry extract exhibits collagen stabilizing activity and reduces capillary permeability and fragility. A standardized extract of bilberry contains at least 25% anthocyanoside content. The remaining components of the oral regimen have been described above.

Advantageously, the compositions of the present invention for topical application and the regimen of supplements are nontoxic vitamins and natural plants extracts which are safe at the dosage levels described herein. Thus, the compositions for hemorrhoid treatment and relief of the present invention provide for temporary relief of pain and discomfort while actively promoting healing through correcting deficiencies.

It is to be understood that the present invention is not limited to the sole embodiments described above, but encompasses any and all embodiments within the scope of the following claims.

I claim:

1. A topical composition for hemorrhoid treatment and relief comprising:
   a) a plant derivative for the enhancement of the formation of collagen and elastin consisting of from about 40 to 100 mg gotu kola extract;
   b) an antioxidant having a proanthocyanidin as the active agent consisting of from about 40 to 100 mg grape seed extract;
   c) an anti-inflammatory agent consisting of about 40 to 100 mg horse chestnut extract and about 40 to 100 mg weight aloe vera gel;
   d) from about 30 to 60 mg vitamin C; and
   e) from about 50 to 200 IU vitamin E.

2. An oral composition for hemorrhoid treatment and relief and the healing of hemorrhoids through replenishing deficiencies, comprising:
   a) between about 100 to 300 mg of gotu kola extract standardized to contain at least 10% asiaticoside;
   b) between about 100 to 300 mg of grape seed extract standardized to contain between about 92 to 95% proanthocyanidins;
   c) between about 100 to 300 mg of bilberry extract standardized to contain at least 25% anthocyanside;
   d) between about 250 to 1,000 mg of vitamin C; and
   e) between about 250 to 1,000 International Units of vitamin E.

3. A composition for topical hemorrhoid treatment and relief, comprising:
   a) about 40 to 100 mg gotu kola extract standardized to contain at least 10% asiaticoside;
   b) about 40 to 100 mg grape seed extract standardized to contain between about 92 to 95% proanthocyanidins;
   c) about 40 to 100 mg horse chestnut extract standardized to contain about 2% aescin;
   d) about 40 to 100 mg aloe vera gel;
   e) about 30 to 60 mg vitamin C; and
   f) about 50 to 200 IU vitamin E.

4. The composition for topical hemorrhoid treatment and relief according to claim 3, further comprising a few drops each of Essential Oil of Chamomile and Essential Oil of Lavender.

5. The composition according to claim 1 formulated in the form of an ointment, a cream or a gel.

6. The composition according to claim 2 formulated in the form of a tablet, a capsule, a softgel or a gelcap.

7. A method for the treatment of hemorrhoids, comprising:
   topically applying to hemorrhoidal areas an effective amount of a composition defined by claim 1; and
   orally administering a composition defined by claim 2.

8. A method for the treatment of hemorrhoids, comprising:
   topically applying to hemorrhoidal areas an effective amount of a composition defined by claim 3; and
   orally administering a composition defined by claim 2.

* * * * *